(12) United States Patent
Liang et al.

(10) Patent No.: US 10,768,316 B2
(45) Date of Patent: Sep. 8, 2020

(54) SILICON CARBIDE SINGLE CRYSTAL X-RAY DETECTOR AND PREPARATION METHOD

(71) Applicant: Dalian University of Technology, Dalian (CN)

(72) Inventors: Hongwei Liang, Dalian (CN); Xiaochuan Xia, Dalian (CN); Heqiu Zhang, Dalian (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 0 days.

(21) Appl. No.: 16/469,600

(22) PCT Filed: Apr. 12, 2018

(86) PCT No.: PCT/CN2018/082778
§ 371 (c)(1),
(2) Date: Jun. 13, 2019

(87) PCT Pub. No.: WO2019/196050
PCT Pub. Date: Oct. 17, 2019

(65) Prior Publication Data
US 2020/0233103 A1     Jul. 23, 2020

(51) Int. Cl.
*G01T 1/24*      (2006.01)
*H01L 31/18*     (2006.01)
*H01L 31/0312*   (2006.01)
*H01L 31/0224*   (2006.01)
*H01L 31/115*    (2006.01)

(52) U.S. Cl.
CPC ........ *G01T 1/24* (2013.01); *H01L 31/022408* (2013.01); *H01L 31/0312* (2013.01); *H01L 31/115* (2013.01); *H01L 31/1812* (2013.01)

(58) Field of Classification Search
CPC ... G01T 1/24; H01L 31/1812; H01L 31/0312; H01L 31/115
See application file for complete search history.

(56) References Cited

U.S. PATENT DOCUMENTS

2009/0096053 A1*  4/2009  Tsuchida ........... H01L 29/66143
                                                                    257/486

FOREIGN PATENT DOCUMENTS

| CN | 104465676 A | * | 3/2015 |
| CN | 104465676 A |   | 3/2015 |

(Continued)

*Primary Examiner* — Mark R Gaworecki
(74) *Attorney, Agent, or Firm* — Muncy, Geissler, Olds & Lowe, P.C.

(57) ABSTRACT

An X-ray detector based on silicon carbide single crystal as well as its preparation method. The detector mainly includes: high resistivity silicon carbide single crystal, high electron concentration n-type silicon carbide layer, low electron concentration n-type silicon carbide layer, high hole concentration p-type silicon carbide layer, low hole concentration p-type silicon carbide layer, silicon dioxide protection layer, p-type silicon carbide ohmic contact electrode, n-type silicon carbide ohmic contact electrode, and gold lead electrode. The invention provides an effective and simple process manufacturing technology, solves the preparation problem of silicon carbide-based high-energy X-ray detector, and realizes the development of a new silicon carbide radiation detector.

4 Claims, 4 Drawing Sheets

(56) References Cited

FOREIGN PATENT DOCUMENTS

| | | |
|---|---|---|
| CN | 107068800 A | 8/2017 |
| JP | 0210141257 A | 6/2010 |
| JP | 2018043907 A | 3/2018 |

* cited by examiner

SILICON CARBIDE SINGLE CRYSTAL X-RAY DETECTOR AND PREPARATION METHOD

TECHNICAL FIELD

The invention belongs to the field of semiconductor device preparation technology, and relates to an X-ray detector based on silicon carbide single crystal as well as its preparation method.

BACKGROUND

The third generation wide band gap semiconductor materials represented by silicon carbide have many outstanding advantages, such as wide band gap, high breakdown electric field, high electron saturation drift speed, corrosion resistance and irradiation resistance. It has important applications in the fabrication of high-efficiency ultraviolet detectors, gas sensors, friendly biosensors, and high-frequency, high-power, anti-radiation and other electronic devices.

In particular, silicon carbide has a band gap of 3.2 eV, a breakdown electric field of $3.0\times10^6$ V/cm, an ionization energy of 7.78 eV, a resistivity of $10^{12}\Omega$.cm, a melting point of 2700° C. and an electron saturation velocity of $2.0\times10^7$ cm/s. It is an ideal material for developing semiconductor radiation detectors.

Several methods have been mastered for preparing silicon carbide single crystals. The conductive properties of n-type and p-type silicon carbide can be achieved by ion implantation. Semi-insulating silicon carbide can be prepared by doping vanadium during the growth process. According to the reported research results, silicon carbide materials are mainly used to prepare power electronic devices and photoelectric devices.

At present, silicon carbide related X-ray detectors with higher performance requirements (the dark current and carrier transmission loss should be as small as possible) are mainly fabricated by homogeneous epitaxy methods.

Due to the limitation of the existing technical conditions, the thickness of the detection sensitive zone of the silicon carbide X-ray detector, which is prepared by the epitaxy growth method, will not exceed 150 microns. For the X-ray has strong penetration, this thickness cannot make the high energy X-ray deposit sufficiently. It directly affects the X-ray detection sensitivity, detection efficiency and the energy resolution, or directly lead to the inability to detect high-energy X-ray.

However, compared with the structure of epitaxy grown silicon carbide devices, the advantages of using silicon carbide single crystal to develop X-ray detectors are as follows: 1. the thickness of single crystal can be cut to meet the needs of high-energy X-ray detection; 2. the high quality of single crystal is conducive to the carrier's effective collection. To this end, the invention proposes using silicon carbide single crystal for the development of X-ray detectors.

SUMMARY

The object of this invention is to propose an X-ray detector based on silicon carbide single crystal as well as its preparation method.

The technical proposal of the invention:

An X-ray detector based on silicon carbide single crystal is proposed, which includes high resistivity silicon carbide single crystal 1, high electron concentration n-type silicon carbide layer 2, low electron concentration n-type silicon carbide layer 3, high hole concentration p-type silicon carbide layer 4, low hole concentration p-type silicon carbide layer 5, silicon dioxide protection layer 6, p-type silicon carbide ohmic contact electrode 7, n-type silicon carbide ohmic contact electrode 8 and gold lead electrode 9.

The high resistance silicon carbide single crystal 1 is the main structure;

The n-type silicon carbide layer 2 with high electron concentration is embedded on the upper surface of the high resistivity silicon carbide single crystal 1, and the upper surface of the two layers is even;

The low electron concentration n-type silicon carbide layer 3 is arranged around the high electron concentration n-type silicon carbide layer 2;

The silicon dioxide protective layer 6 is arranged around the n-type silicon carbide ohmic contact electrode 8, and it is integrally covered on the upper surface of the high resistance silicon carbide single crystal 1;

The two gold lead electrodes 9 are located on the upper surface of the junction of the silicon oxide protective layer 6 and the n-type silicon carbide ohmic contact electrode 8;

The high hole concentration p-type silicon carbide layer 4 is embedded on the lower surface of the high resistivity silicon carbide single crystal 1, and the upper surface of the two layers is even;

The low hole concentration p-type silicon carbide layer 5 is arranged around the high hole concentration p-type silicon carbide layer 4;

The p-type silicon carbide ohmic contact electrode 7 is an inverted T-type, and the top contacts with the high hole concentration p-type silicon carbide layer 4;

The gap between the low hole concentration p-type silicon carbide layer 5 and the p-type silicon carbide ohmic contact electrode 7 is filled with a silicon dioxide protective layer 6, covering the lower surface of the high resistance silicon carbide single crystal 1.

The preparation steps are as follows.

Step 1: Graphical AlN ion implantation barrier layers were prepared on the upper and lower surfaces of high resistive silicon carbide single crystal 1 by photolithographic mask assistant deposition. The barrier layers were AlN ion implantation barrier layer a10, AlN ion implantation barrier layer b11 and AlN ion implantation barrier layer c12. The thickness of the barrier layer a10 was 10 nm to 10 μm, and the diameter of the barrier layer a10 was 50%~90% of the edge length of the whole sample. The thickness of layer b11 is 10 nm~15 μm, and the annular width accounts for 5%~30% of the edge length of the whole sample. The thickness of layer c12 is 10 nm~20 μm, covering all areas except for the a10 and b11.

Step 2: An n-type silicon carbide layer with transverse distribution of electron concentration and a p-type silicon carbide layer with transverse distribution of hole concentration were respectively formed on the upper and lower surface of high-resistivity silicon carbide crystal 1 by ion implantation and thermal annealing; the thickness of n-type silicon carbide layer and p-type silicon carbide layer was 10 nm to 10 μm; the n-type silicon carbide layer consisted of high-electron concentration n-type silicon carbide layer 2 and low-electron concentration n-type silicon carbide layer 3, the low electron concentration n-type silicon carbide layer 3 are arranged around electron concentration n-type silicon carbide layer 2, electron concentration of the high electron concentration n-type silicon carbide layer 2 is $5.0\times10^{16}$ $cm^{-3}$~$5.0\times10^{19}$ $cm^{-3}$, and electron concentration of low electron concentration n-type silicon carbide layer 3 is $5.0\times10^{15}$ cm$^{-3}$~$5.0\times10^{18}$ cm$^{-3}$; p-type silicon carbide layer includes high hole concentration p-type silicon carbide layer 4 and low hole concentration p-type silicon carbide layer 5, the low hole concentration p-type silicon carbide layer 5 is arranged around high hole concentration p-type silicon carbide layer 4, the hole concentration of high hole concentration p-type silicon carbide layer 4 is $5.0\times10^{16}$ cm$^{-3}$~$5.0\times10^{19}$ cm$^{-3}$, and the hole concentration of low hole concentration p-type silicon carbide layer 5 is $5.0\times10^{15}$ cm$^{-3}$~$5.0\times10^{18}$ cm$^{-3}$.

Step 3: Protect the AlN layer on the upper surface of SiC crystal 1, wet etch the AlN layer on the lower surface of SiC crystal 1, deposit Silicon dioxide layer 6 on the lower surface of SiC crystal 1, use photolithography mask technology and HF wet etching technology to open holes on the Silicon dioxide protection layer 6, use photolithography mask technology, deposition technology and thermal annealing technology to prepare p-type silicon carbide ohmic junction contact electrode 7;

Among them, the thickness of Silicon dioxide protective layer 6 is 10 nm~10 μm, the area of the open hole is the same as that of high hole concentration p-type SiC layer 4, and the thickness of p-type SiC ohmic contact electrode 7 is 10 nm~15 μm, and the width is between the edge of open hole and the edge of the lower surface of SiC single crystal 1.

Step 4: Wet etching of AlN layer on the surface of silicon carbide single crystal 1, depositing Silicon dioxide protective layer 6 on the surface of silicon carbide single crystal 1; using photolithographic mask technology and HF wet etching technology to open holes on Silicon dioxide protective layer 6; using photolithographic mask technology and coating technology to prepare patterned n-type silicon carbide ohmic contact electrode 8; using photolithographic mask technology, deposition technology and thermal annealing technology to fabricate of graphical gold lead electrode 9;

Among them, the thickness of silicon dioxide protective layer 6 is 10 nm~10 μm; the area of open hole is the same as that of high electron concentration n-type silicon carbide layer 2; the thickness of n-type silicon carbide ohmic contact electrode 8 is 10 nm~15 μm, and the area of open hole is the same; the thickness of gold lead electrode 9 is 10 nm~10 μm, and the coverage area is between 10% of the surface edge of the high resistivity silicon carbide single crystal 1.

The corrosive solution is one or two mixtures of sodium hydroxide and potassium hydroxide.

The deposition methods are sol-gel method, thermal evaporation method, electron beam evaporation method, magnetron sputtering method, laser pulse deposition, atomic layer epitaxy or molecular beam epitaxy.

Beneficial effect of the invention: The invention designs a new X-ray detector structure based on silicon carbide single crystal, and proposes an effective and simple process manufacturing technology, which solves the preparation problem of silicon carbide-based high-energy X-ray detector and realizes the development of a new silicon carbide radiation detector.

Figure 1:
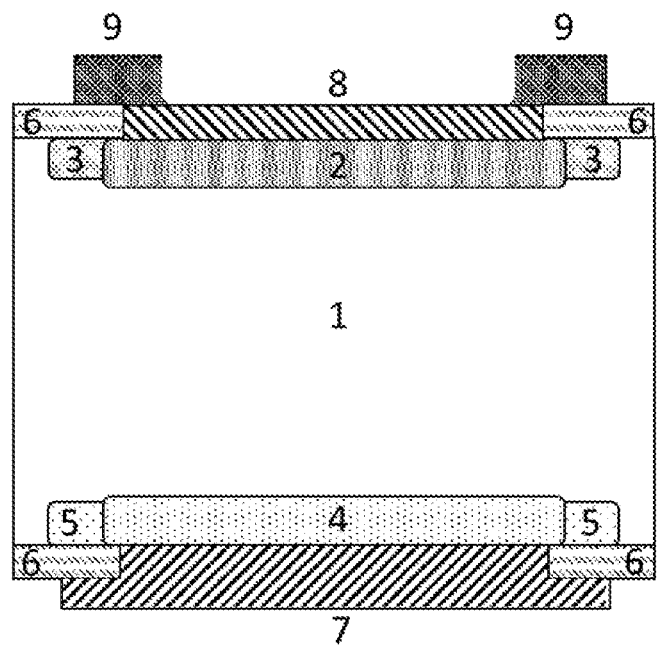
FIG. 1 is a schematic diagram of an X-ray detector based on silicon carbide single crystal.
Figure 2:
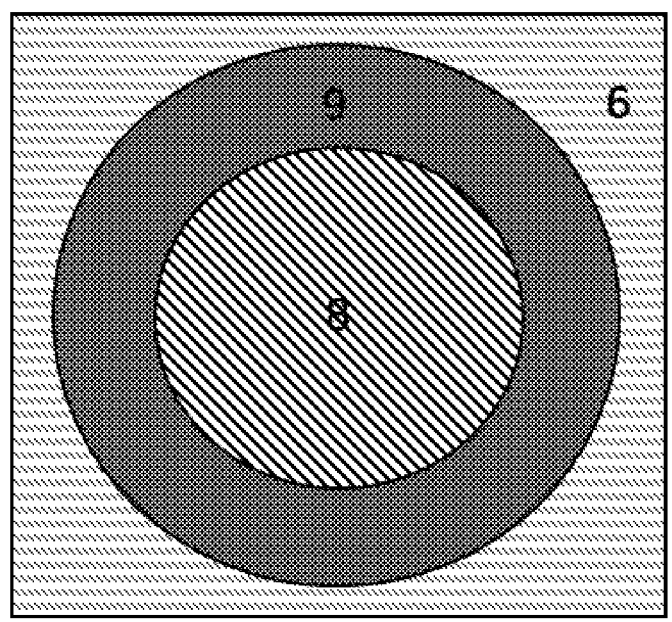
FIG. 2 is a top view of the device structure with an n-type silicon carbide contact electrode.
Figure 3:
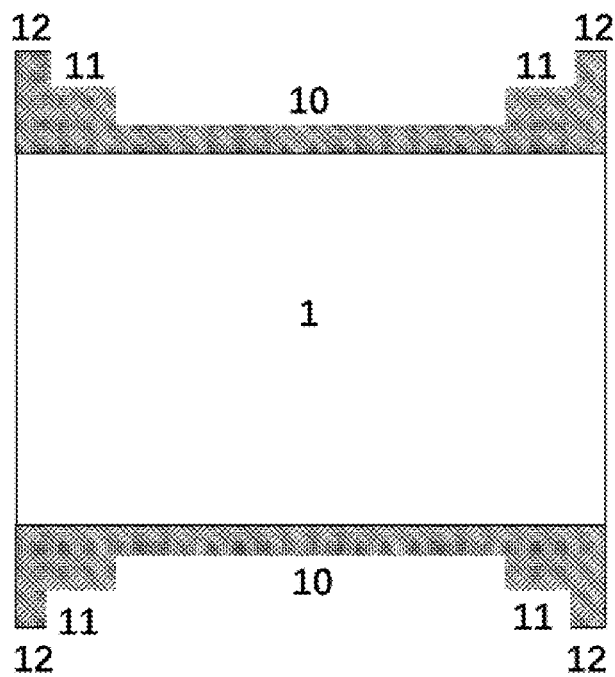
FIG. 3 is a cross-sectional diagram of silicon carbide single crystal with an AlN ion implantation barrier layer.
Figure 4:
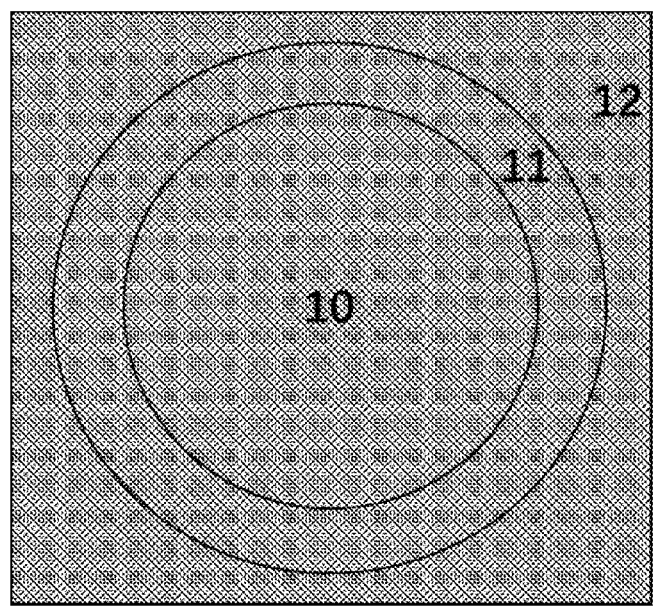
FIG. 4 is a graphic illustration of silicon carbide single crystal with an AlN ion implantation barrier layer.
Figure 5:
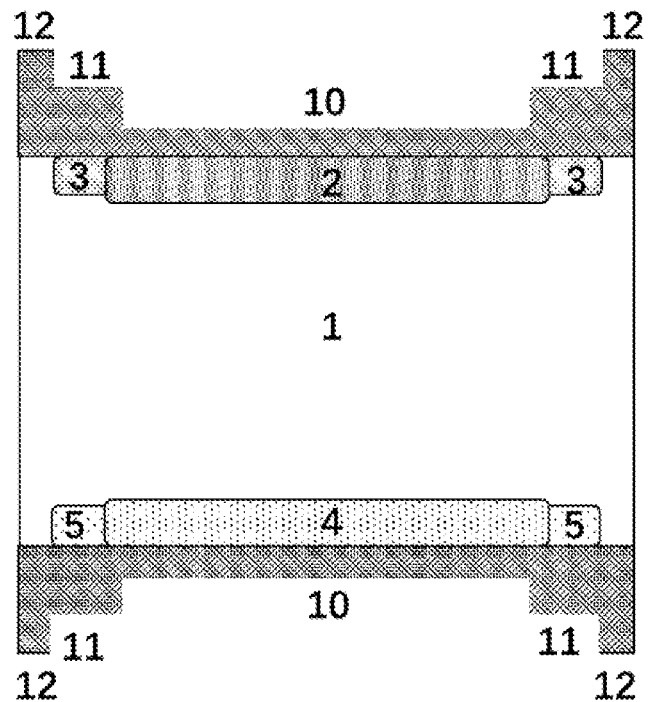
FIG. 5 is a schematic diagram of silicon carbide single crystal with AlN barrier layer after ion implantation and thermal annealing.
Figure 6:
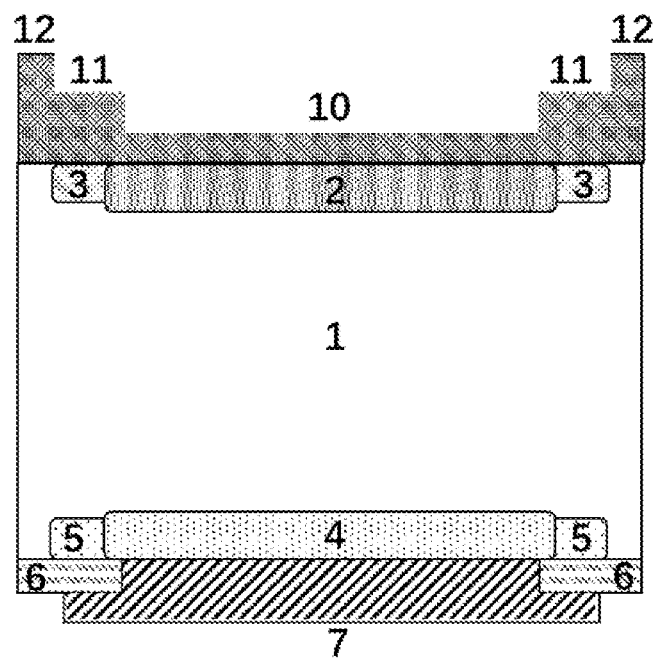
FIG. 6 is a cross-sectional diagram of a device with a p-type silicon carbide contact electrode.
Figure 7:
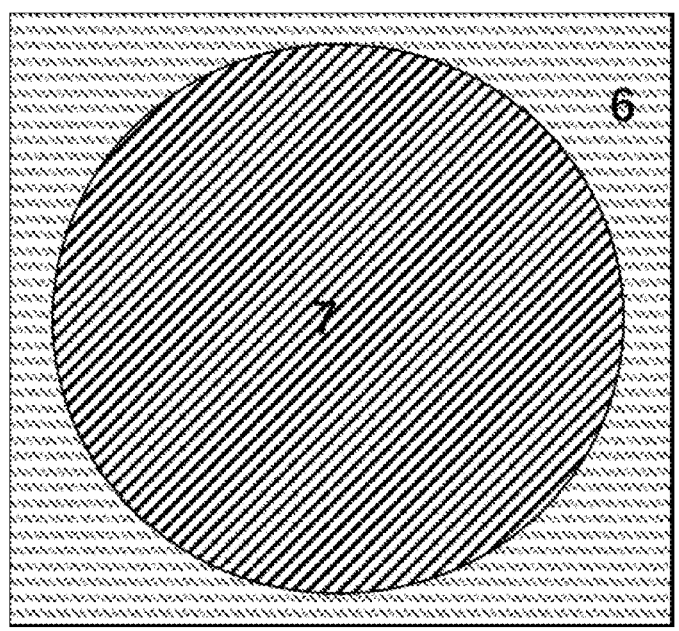
FIG. 7 is a schematic diagram of the device structure with a p-type silicon carbide contact electrode.

Figure: 1 high resistance silicon carbide single crystal; 2 high electron concentration n-type silicon carbide layer; 3 low electron concentration n-type silicon carbide layer; 4 high hole concentration p-type silicon carbide layer; 5 low hole concentration p-type silicon carbide layer; 6 silicon dioxide protective layer; 7 p-type silicon carbide ohmic contact electrode; 8 n-type silicon carbide ohmic contact electrode; 9 gold lead electrode; 10 AlN ion implantation barrier layer a; 11 AlN ion implantation barrier layer b; 12 AlN ion implantation barrier layer c.

DETAILED DESCRIPTION

A detailed operation method of the invention is further illustrated with the following figures and technical plans.

EXAMPLE 1

This example provides a method for proposing an X-ray detector based on silicon carbide single crystal, including the following process steps:

Step 1: Select high resistivity silicon carbide single crystals with thickness of 200 um and surface of 5 mm square.

Step 2: Graphical AlN ion implantation barrier layer was prepared on the upper and lower surfaces of high resistive silicon carbide single crystal 1 by multiple photolithographic mask assisted deposition. The thickness of AlN ion implantation barrier layer a10 is 50 nm and its diameter is 3 mm; the thickness of AlN ion implantation barrier layer b11 is 100 nm and its ring width is 0.5 mm; and the thickness of AlN ion implantation barrier layer c12 is 500 nm.

Step 3: An n-type silicon carbide layer with transverse distribution of electron concentration and a p-type silicon carbide layer with transverse distribution of hole concentration were formed on the upper and lower surface of high-resistivity silicon carbide crystal 1 by ion implantation and thermal annealing; the thickness of high electron concentration n-type silicon carbide layer 2 and high hole concentration p-type silicon carbide layer 4 are 400 nm. The electron concentration of the high electron concentration n-type silicon carbide layer 2 is $1.0\times10^{18}$ cm$^{-3}$. The hole concentration of the high hole concentration p-type silicon carbide layer 4 is $5.0\times10^{17}$ cm$^{-3}$; the thickness of low electron concentration n-type silicon carbide layer 3 and low hole concentration p-type silicon carbide layer 5 are 350 nm. The electron concentration of the low electron concentration n-type silicon carbide layer 3 is $5.0\times10^{17}$ cm$^{-3}$. The hole concentration of the low hole concentration p-type silicon carbide layer 5 is $1.0\times10^{17}$ cm$^{-3}$;

Step 4: Use wax to protect the AlN layer on the upper surface, use potassium hydroxide solution to corrode the AlN layer on the lower surface, deposit silicon dioxide protective layer 6; then use photolithography mask technology and HF wet etching technology to open holes on silicon dioxide protective layer 6; and then use photolithography mask technology, deposition technology and thermal annealing technology to prepare p-type ohmic contact electrode; The thickness of silicon dioxide protective layer 6 is 100 nm, the aperture diameter is 3 mm, the thickness of p-type silicon carbide ohmic contact electrode 7 is 200 nm and its diameter is 4 mm.

Step 5: AlN layer on the upper surface was eroded by potassium hydroxide solution, and deposited silicon dioxide protective layer 6; then the photolithographic mask technology and HF wet etching technology were used to open holes on silicon dioxide protective layer 6; the n-type silicon carbide ohmic contact electrode 8 was fabricated by photolithographic mask technology and deposition technology; the thickness of silicon dioxide protective layer 6 was 100 nm; the diameter of the hole was 3 mm; The thickness of n-type silicon carbide ohmic contact electrode 8 is 100 nm and its diameter is 3 mm. Then the annular gold lead electrode 9 is prepared by photolithography mask technology, coating technology and thermal annealing technology. The outer ring diameter is 4 mm, the inner ring diameter is 2.6 mm, and the thickness is 500 nm.

The invention claimed is:

1. A silicon carbide single crystal X-ray detector, composed of a high resistivity silicon carbide single crystal, a high electron concentration n-type silicon carbide layer, a low electron concentration n-type silicon carbide layer, a high hole concentration p-type silicon carbide layer, a low hole concentration p-type silicon carbide layer, a silicon dioxide protection layer, a p-type silicon carbide ohmic contact electrode, an n-type silicon carbide ohmic contact electrode and a gold lead electrode;

wherein the high resistance silicon carbide single crystal is the main structure; the n-type silicon carbide layer with high electron concentration is embedded on an upper surface of the high resistivity silicon carbide single crystal, and an upper surface of the two layers is even; the low electron concentration n-type silicon carbide layer is arranged around the high electron concentration n-type silicon carbide layer; the silicon dioxide protective layer is arranged around the n-type silicon carbide ohmic contact electrode, and it is integrally covered on the upper surface of the high resistance silicon carbide single crystal; the two gold lead electrodes are located on an upper surface of the junction of the silicon dioxide protective layer and the n-type silicon carbide ohmic contact electrode;

the high hole concentration p-type silicon carbide layer is embedded on a lower surface of the high resistivity silicon carbide single crystal, and the upper surface of the two layers is even; the low hole concentration p-type silicon carbide layer is arranged around the high hole concentration p-type silicon carbide layer; the p-type silicon carbide ohmic contact electrode is an inverted T-type, and the top contacts with the high hole concentration p-type silicon carbide layer; a gap between the low hole concentration p-type silicon carbide layer and the p-type silicon carbide ohmic contact electrode is filled with the silicon dioxide protective layer, covering the lower surface of the high resistance silicon carbide single crystal.

2. A preparation method for a silicon carbide single crystal X-ray detector, comprising the following steps:

step 1: graphical AlN ion implantation barrier layers were prepared on upper and lower surfaces of a high resistive silicon carbide single crystal by photolithographic mask assistant deposition; the barrier layers were AlN ion implantation barrier layer a10, AlN ion implantation barrier layer b11 and AlN ion implantation barrier layer c12; a thickness of the barrier layer a10 was 10 nm to 10 μm, and a diameter of the barrier layer a10 was 50%~90% of an edge length of a whole sample; a thickness of layer b11 is 10 nm~15 μm, and an annular width accounts for 5%~30% of the edge length of the whole sample; a thickness of layer c12 is 10 nm~20 μm, covering all areas except for the a10 and b11;

step 2: an n-type silicon carbide layer with transverse distribution of electron concentration and a p-type silicon carbide layer with transverse distribution of hole concentration were formed on an upper and lower surface of high-resistivity silicon carbide crystal by ion implantation and thermal annealing; a thickness of the n-type silicon carbide layer and the p-type silicon carbide layer was 10 nm to 10 μm; the n-type silicon carbide layer consisted of a high-electron concentration n-type silicon carbide layer and a low-electron concentration n-type silicon carbide layer, the low electron concentration n-type silicon carbide layer are arranged around the electron concentration n-type silicon carbide layer, an electron concentration of the high electron concentration n-type silicon carbide layer is $5.0 \times 10^{16}$ cm$^{-3}$~$5.0 \times 10^{19}$ cm$^{-3}$, and an electron concentration of the low electron concentration n-type silicon carbide layer is $5.0 \times 10^{15}$ cm$^{-3}$~$5.0 \times 10^{18}$ cm$^{-3}$; the p-type silicon carbide layer includes a high hole concentration p-type silicon carbide layer and a low hole concentration p-type silicon carbide layer, the low hole concentration p-type silicon carbide layer is arranged around the high hole concentration p-type silicon carbide layer, a hole concentration of the high hole concentration p-type silicon carbide layer is $5.0 \times 10^{16}$ cm$^{-3}$~$5.0 \times 10^{19}$ cm$^{-3}$, and a hole concentration of the low hole concentration p-type silicon carbide layer is $5.0 \times 10^{15}$ cm$^{-3}$~$5.0 \times 10^{18}$ cm$^{-3}$;

step 3: protect the AlN layer on the upper surface of SiC crystal, wet etch the AlN layer on the lower surface of SiC crystal, deposit a silicon dioxide layer on the lower surface of SiC crystal, use photolithography mask technology and HF wet etching technology to open holes on a silicon dioxide protection layer, use photolithography mask technology, deposition technology and thermal annealing technology to prepare a p-type silicon carbide ohmic junction contact electrode;

among them, the thickness of the silicon dioxide protective layer is 10 nm~10 μm, the area of the open hole is the same as that of the high hole concentration p-type SiC layer 4, and a thickness of p-type SiC ohmic contact electrode is 10 nm~15 μm, and a width is between an edge of the open hole and an edge of the lower surface of SiC single crystal;

step 4: wet etching of the AlN layer on the surface of silicon carbide single crystal, depositing silicon dioxide protective layer on the surface of the silicon carbide single crystal; using photolithographic mask technology and HF wet etching technology to open holes on the silicon dioxide protective layer; using photolithographic mask technology and coating technology to prepare a patterned n-type silicon carbide ohmic contact electrode; using photolithographic mask technology, deposition technology and thermal annealing technology to fabricate of a graphical gold lead electrode;

among them, a thickness of silicon dioxide protective layer is 10 nm~10 μm; the area of open hole is the same as that of high electron concentration n-type silicon carbide layer; a thickness of n-type silicon carbide ohmic contact electrode is 10 nm~15 μm, and the area of open hole is the same; a thickness of gold lead electrode is 10 nm~10 μm, and a coverage area is between 10% of a surface edge of the high resistivity silicon carbide single crystal.

3. The preparation method of claim 2, wherein the corrosive solution is one or two mixtures of sodium hydroxide and potassium hydroxide.

4. The preparation method of claim 2, wherein the deposition methods are sol-gel method, thermal evaporation method, electron beam evaporation method, magnetron sputtering method, laser pulse deposition, atomic layer epitaxy or molecular beam epitaxy.

* * * * *